(12) United States Patent
Seyfang (10) Patent No.: US 6,878,531 B1
(45) Date of Patent: Apr. 12, 2005

(54) METHOD FOR MULTIPLE SITE-DIRECTED MUTAGENESIS

(75) Inventor: Andreas Seyfang, Augusta, GA (US)

(73) Assignee: Medical College of Georgia Research Institute, Augusta, GA (US)

( * ) Notice: Subject to any disclaimer, the term of this patent is extended or adjusted under 35 U.S.C. 154(b) by 0 days.

(21) Appl. No.: 10/766,190

(22) Filed: Jan. 29, 2004

Related U.S. Application Data

(60) Provisional application No. 60/518,319, filed on Nov. 10, 2003.

(51) Int. Cl.[7] .............................................. C12P 19/34
(52) U.S. Cl. ...................................... 435/91.2; 435/91.1
(58) Field of Search ................................ 435/91.1, 91.2

(56) References Cited

U.S. PATENT DOCUMENTS 6,676,924 B2 * 1/2004 Hansen et al. ............. 424/1.49

OTHER PUBLICATIONS

Kunkel, "Rapid and efficient site–specific mutagenesis without phenotypic selection," *Proc. Natl. Acad. Sci.*, vol. 82, pp 488–492, Jan. 1985.
Weiner et al., "Site–directed Mutagenesis of double–stranded DNA by the polymerase chain reaction," *Gene.*, vol. 151, pp 119–123, 1994.
Ishii et al., "Site–Directed Mutagenesis," *Methods in Enzymology*, vol. 293, pp 53–71, 1998.
Mikaelian et al., "A general and fast method to generate multiple site directed mutations," *Nucleic Acids Research*, vol. 20, No. 2, p. 376, 1992.
Dwivedi et al., "Generation of Multiple Mutations in the Same Sequence via the Polymerase Chain Reaction Using a Single Selection Primer," *Analytical Biochemistry*, vol. 221, pp 425–428, 1994.

Bhat, "Multiple Site–Directed Mutagenesis," *Methods in Molecular Biology*, vol. 57, pp 269–277, 1996.
Meetei et al., "Generation of Multiple Site–Specific Mutations in a Single Polymerase Chain Reaction Product," *Analytical Biochemistry*, vol. 264, pp 288–291, 1998.
Kim et al., "Multiple Site Mutagenesis with High Targeting Efficiency in One Cloning Step," *BioTechniques*, vol. 28., No. 2, pp 196–198, 2000.
Lee et al., "Multiple Mutagenesis of non–universal serine codons of the *Candida rugos* LIP2 gene and biochemical characterization of purified recombinant LIP2 lipase over–expressed in *Pichia pastoris*," *Biochem. J.*, vol. 366, pp 603–611, 2002.
Javitch et al., "Use of the Substituted Cysteine Accessibility Method to Study the Structure and Function of G Protein–Coupled Receptors," *Methods in Enzymology*, vol. 343, pp 137–156, 2002.

(Continued)

*Primary Examiner*—James Ketter
*Assistant Examiner*—Tara L. Garvey
(74) *Attorney, Agent, or Firm*—Jagtiani + Guttag (57) ABSTRACT

The present invention provides a simple and rapid method for site-directed mutagenesis of more than, for example, 10 sites simultaneously with up to 100% efficiency. The method uses two terminal tailed primers, specific for each end of the gene (or DNA sequence) to be mutated, with a unique nucleotide tail each that are simultaneously annealed to template DNA together with a set of mutagenic primers in-between. Following synthesis of the mutant strand by primer extension and ligation with, for example, T4 DNA polymerase and ligase, the unique mutant strand-specific tails of the terminal primers are used as anchors to specifically amplify the mutant strand by high-fidelity polymerase chain reaction. Furthermore, specific restriction endonuclease sites in the two anchor primer tails may be used for convenient subcloning of the PCR product in any desired cloning or expression vector (for subsequent sequencing or expression and functional studies of the mutated gene).

52 Claims, 2 Drawing Sheets

OTHER PUBLICATIONS

Danielson et al., "Cysteine and Disulfide Scanning Reveals a Regulatory α–Helix in the Cytoplasmic Domain of the Aspartate Receptor," *The Journal of Biological Chemistry,* vol. 272, No. 52, pp 32878–32888, Dec. 1997.

Cruz et al., "Double targeted gene replacement for creating null mutants," *Proc. Natl. Acad. Sci.,* vol. 88, pp 7170–7174, Aug. 1991.

Seyfang et al., "Aspartate 19 and Glutamate 121 Are Critical for Transport Function of the myo–Inositol/H+ Symporter from *Leishmania donovani*," *The Journal of Biological Chemistry,* vol. 272, No. 39, pp 24210–24215, Sep. 1997.

Jin et al., "High–affinity myo–inositol transport in *Candida albicans*: substrate specificity and pharmacology," *Microbiology,* vol. 149, pp 3371–3381, 2003.

Thompson et al., "An Improved Protocol for the Preparation of Yeast Cells for Transformation by Electroporation," *Yeast,* vol. 14, pp 565–571, 1998.

Ausubel et al., "Introduction of DNA into Yeast Cells," *Short Protocols in Molecular Biology, Fourth Edition,* Unit 13.7, pp 13.31–13.36, 1999.

Medina–Acosta et al., "Rapid isolation of DNA from trypanosomatid protozoa using a simple 'mini–prep' procedure," *Molecular and Biochemical Parasitology,* vol. 59, pp 327–330, 1993.

Kunkel et al., "On the Fidelity of DNA Replication," *The Journal of Biological Chemistry,* vol. 259, No. 3, pp 1539–1545, Feb. 1984.

Tindall et al., "Fidelity of DNA Synthesis by the *Thermus aquaticus* DNA Polymerase," *Biochemistry,* vol. 27, pp 6008–6013, 1988.

Cline et al., "PCR fidelity of Pfu DNA polymerase and other thermostable DNA polymerases," *Nucleic Acids Research,* vol. 24, No. 18, pp 3546–3551, 1996.

Santos et al., "Transfer RNA structural change is a key element in the reassignment of the CUG codon in *Candida albicans*," *The EMBO Journal,* vol. 15, No. 18, pp 5060–5068, 1996.

Kong et al., "Characterization of a DNA Polymerase from the Hyperthermophile Archaea *Thermococcus litoralis*," *The Journal of Biological Chemistry,* vol. 268, No. 3, pp 1965–1975, Jan. 1993.

Cohen et al., "Functional expression of rat GLUT 1 glucose transporter in *Dictyostelium discoideum*," *Biochem J.,* vol. 315, pp 971–975, 1996.

Sawano et al., "Directed evolution of green fluorescent protein by a new versatile PCR strategy for site–directed and semi–random mutagenesis," *Nucleic Acids Research,* vol. 28, No. 16, pp. i–vii, 2000.

\* cited by examiner

METHOD FOR MULTIPLE SITE-DIRECTED MUTAGENESIS

CROSS-REFERENCE TO RELATED APPLICATIONS

This application makes reference to and claims priority to U.S. Provisional Patent Application No. 60/518,319, entitled "Method for Multiple Site-Directed Mutagenesis," filed Nov. 10, 2003, the entire contents and disclosure of which is hereby incorporated by reference.

BACKGROUND OF THE INVENTION

1. Field of the Invention

The present invention relates generally to a method for site-directed mutagenesis and more particularly to a method for site-directed mutagenesis of more than, for example, 10 sites simultaneously with up to 100% efficiency.

2. Description of the Prior Art

Site-directed mutagenesis is a powerful tool to explore the structure-function relationship of proteins, but most traditional methods rely on the mutation of only one site at a time and efficiencies drop drastically when more than three sites are targeted simultaneously. Many applications in functional proteomics and genetic engineering, including codon optimization for heterologous expression, generation of cysteine-less proteins or alanine-scanning mutagenesis, would greatly benefit from a multiple-site mutagenesis method with high efficiency.

Probing the structure-function relationship of proteins and nucleic acids by site-directed mutagenesis has become an important strategy in functional studies and genetic engineering, see J. Braman (Ed.), In Vitro Mutagenesis Protocols, Methods in Molecular Biology, Vol. 182, 2nd Ed, Humana Press, Totowa, 2002, the entire contents and disclosure of which is hereby incorporated by reference. In site-directed mutagenesis, the genetic code for a protein is altered at a specific site by changing one (or multiple) of the individual nucleotides that make up a gene and that code for a specific protein. A variety of very efficient methods have become available for site-directed mutagenesis of individual sites, both PCR-based and non-PCR-based, and several convenient commercial kits are on the market, see T. A. Kunkel, Rapid and efficient site-specific mutagenesis without phenotype selection, Proc. Natl. Acad. Sci. USA, 82 (1985) pp. 488–492; M. P. Weiner, G. L. Costa, W. Schoettlin, J. Cline, E. Mathur, J. C. Bauer, Site-directed mutagenesis of double-stranded DNA by the polymerase chain reaction, Gene, 151 (1994) pp. 119–123; and T. M. Ishii, P. Zerr, X. M. Xia, C. T. Bond, J. Maylie, J. P. Adelman, Site-directed mutagenesis, Methods Enzymol., 293 (1998) pp. 53–71, the entire contents and disclosures of which are hereby incorporated by reference. Most of these methods rely on the mutation of only one site at a time and efficiencies drop drastically when more than three sites are targeted simultaneously. For example, Sawano and Miyawaki provided a protocol that allows for the introduction of mutations at two sites simultaneously with one primer for each mutation site, which required two rounds of PCR amplification separated by an additional DpnI digest of parental DNA. Nevertheless, they achieved an efficiency of 76% for only two mutations, but efficiencies drop further at an exponential rate if more than three sites are targeted in a single step, see A. Sawano and A. Miyawaki, Directed evolution of green fluorescent protein by a new versatile PCR strategy for site-directed and semi-random mutagenesis, Nucleic Acids Research, Vol. 28, No. 16 (2000) p. e78, the entire contents and disclosure of which is hereby incorporated by reference.

Several multiple site-directed mutagenesis methods have also been described, which all require multiple rounds of PCR, including successive rounds of overlap extension PCR or successive rounds of PCR combined with in vitro dam-methylation/ligation before and DpnI digest and gel purification after each PCR step, see I. Michaelian, A. Sergeant, A general and fast method to generate multiple site directed mutations, Nucleic Acids Res., 20 (1992) p. 376; U. N. Dwivedi, N. Shiraishi, W. H. Campbell, Generation of multiple mutations in the same sequence via the polymerase chain reaction using a single selection primer, Anal. Biochem., 221 (1994) pp. 425–428; K. S. Bhat, Multiple site-directed mutagenesis, Methods Mol. Biol., 57 (1996) pp. 269–277; A. R. Meetei, M. R. Rao, Generation of multiple site-specific mutations in a single polymerase chain reaction product, Anal. Biochem., 264 (1998) pp. 288–291; Y. G. Kim, S. Maas, Multiple site mutagenesis with high targeting efficiency in one cloning step, Biotechniques, 28 (2000) pp. 196–198; G. C. Lee, L. C. Lee, V. Sava, J. F. Shaw, Multiple mutagenesis of non-universal serine codons of the *Candida rugosa* LIP2 gene and biochemical characterization of purified recombinant LIP2 lipase overexpressed in *Pichia pastoris*, Biochem. J., 366 (2002) pp. 603–611; and international application numbers WO 03/002761A1 and WO 99/25871, the entire contents and disclosures of which are hereby incorporated by reference. Nevertheless, these methods are complicated by the time requirements for multiple PCR rounds, combined with an increased risk of introducing undesired second-site mutations during extensive use of thermostable polymerases in repeated PCR rounds. Furthermore, most of these methods require two complementary mutagenic primers for each site-directed mutation. Hence, a rapid and efficient multiple-site mutagenesis method would be of great benefit to a variety of applications in functional proteomics and genetic engineering that, for example, require codon optimization for heterologous expression systems, the generation of cysteine-less proteins for subsequent cysteine-scanning mutagenesis and disulfide-scanning mutagenesis studies, or (re)design and removal of restriction endonuclease sites in expression vectors, genes of selectable markers, etc., see J. A. Javitch, L. Shi, G. Liapakis, Use of the substituted cysteine accessibility method to study the structure and function of G protein-coupled receptors, Methods Enzymol., 343 (2002) pp. 137–156; and M. A. Danielson, R. B. Bass, J. J. Falke, Cysteine and disulfide scanning reveals a regulatory alpha-helix in the cytoplasmic domain of the aspartate receptor, J. Biol. Chem., 272 (1997) pp. 32878–32888, the entire contents and disclosures of which are hereby incorporated by reference.

SUMMARY OF THE INVENTION

It is therefore an object of the present invention to provide a method for site-directed mutagenesis of multiple sites with a high level of efficiency.

According to a first broad aspect of the present invention, there is provided a method for site-directed mutagenesis comprising the steps of providing two terminal tailed primers comprising an anchor portion and a portion having nucleotide sequences respectively complementary to each end of a gene to be mutated, annealing the complementary portion of the terminal tailed primers and a set of mutagenic primers to template DNA in a single step; synthesizing a mutant strand by primer extension and ligation; and amplifying the mutant strand by polymerase chain reaction.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 1 is a schematic diagram of multiple site-directed mutagenesis of more than 10 mutations simultaneously according to an embodiment of the present invention. Phosphorylated mutagenic primers are annealed to template DNA (alkali-denatured double-stranded DNA) together with a pair of terminal, tailed anchor primers, which contain a unique nucleotide tail each for subsequent mutant strand-specific PCR. In step 1, mutant strand synthesis is performed by primer extension and ligation with a DNA polymerase and ligase in a single incubation step, which fills all gaps between the primers. In step 2, the mutant strand from step one is amplified by high-fidelity PCR specifically and selectively with the PCR anchor primers complementary to the nucleotide tails introduced by the terminal anchor primers. Only one set of antisense mutagenic primers is needed for this protocol and the efficiency approaches 100% owing in part to a molar excess of mutagenic oligonucleotide primers relative to the pair of terminal anchor primers during primer annealing.

FIG. 2 shows the generation of Neo and Hyg genes with *Candida albicans*-friendly leucine codons by multiple site-directed mutagenesis and subsequent use for targeted gene replacement in *C.albicans*. Panel A shows agarose gel electrophoresis of the PCR products of *C.albicans*-friendly $Neo_{Calb}$ and $Hyg_{Calb}$ genes produced by the mutagenesis protocol outlined in FIG. 1, in which each of the 11 or 9 CUG leucine codons, respectively, was mutated to the *Candida*-compatible UUG leucine codon (7 μL of PCR sample per lane). Panel B shows results using ten microliters of PCR product with the linear CaTP::$Hyg_{Calb}$ knockout construct (2.83 kb) for targeted gene replacement of the *C.albicans* transporter CaTP. Panel C shows identification of heterozygous CaTP knockout cells by PCR performed on genomic DNA isolated from *C.albicans* clone 25 and subclones 25.1 and 25.2, which were transformed with the linear CaTP::$Hyg_{Calb}$ knockout construct and selected on YPD agar plates in the presence of 500 μg/mL hygromycin B. PCR performed on genomic DNA from untransformed *C.albicans* wild-type cells (WT) or on plasmid DNA containing the CaTP::$Hyg_{Calb}$ knockout construct in pBluescript (Hyg) served as control (10 μL of PCR sample per lane). The first lane of each gel contains 5 μL of molecular size DNA markers (HyperLadder 0.2–10 kb; Bioline).

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "simultaneously" refers to events occurring within the same reaction step, i.e. site-directed mutagenesis of multiple sites where all desired mutation sites are targeted/mutated at the same time and in a single reaction step.

Figure 1:
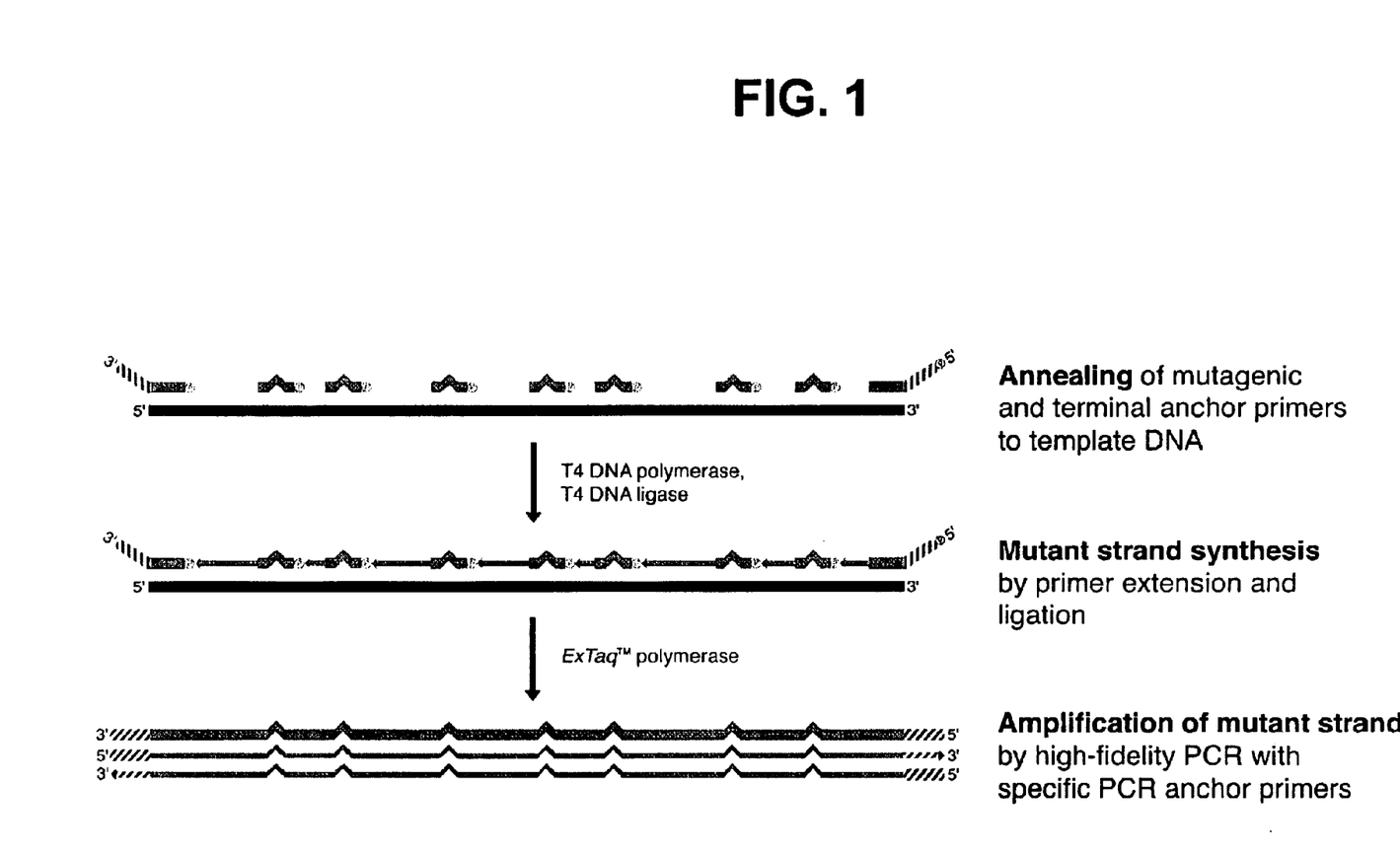

For the purposes of the present invention, the term "terminal tailed primers" refers to a pair of primers specific for the two ends (termini) of the mutated gene, which, in addition to the gene-specific sequence used for the initial annealing, have a nucleotide "tail" of a unique sequence that is not found in the mutated gene or DNA sequence (depicted as a kink and shown with cross-hatching in the terminal two primers shown in FIG. 1). This portion (tail) of the two primers is hence used for the subsequent selective and specific amplification of only the mutated gene (or DNA sequence), to achieve the up to 100% efficiency of the methods of the present invention.

For the purposes of the present invention, the term "complementary" refers to having a nucleotide sequence that is complementary to the opposite DNA strand, which may, in the case of the mutagenic primers, also include sequences of one or multiple nucleotides that are to be mutated from the original sequence and hence are not complementary.

For the purposes of the present invention, the term "restriction endonuclease site" refers to a nucleotide sequence specific for recognition and cutting with a specific restriction endonuclease ("restriction enzyme").

For the purposes of the present invention, the term "mutagenic primer" refers to the primer that introduces the site-specific mutation, i.e. contains a mutation-specific nucleotide mismatch (non-complementary nucleotide sequence) within its nucleotide sequence that is otherwise complementary to a portion of the gene or DNA sequence to be mutated.

Description

The present invention provides a simple and rapid method for site-directed mutagenesis of more than, for example, 10 sites simultaneously with up to 100% efficiency. The method uses two terminal tailed primers, specific for each end of the gene to be mutated, with a unique nucleotide tail each that are simultaneously annealed to template DNA together with a set of mutagenic primers in-between. Following synthesis of the mutant strand by primer extension and ligation with, for example, T4 DNA polymerase and ligase, the unique mutant strand-specific tails of the terminal primers are used as anchors to specifically amplify the mutant strand by high-fidelity polymerase chain reaction. Furthermore, specific restriction endonuclease sites in the two anchor primer tails may be used for convenient subcloning of the PCR product in any desired cloning or expression vector (for subsequent sequencing or expression and functional studies of the mutated gene).

The methods of the present invention provide for site-directed mutagenesis of a plurality of sites, for example, 5, 10 or more than 10 sites simultaneously. The methods of the present invention may by used for mutagenesis of multiple sites, including 20, 30, 40, 50, or more sites, the limiting number being determined primarily by the length of the mutated gene or DNA sequence to be amplified by the high-fidelity PCR step, which, with current enzymes, is approximately 15–20 kbp of length. In addition, while several of the examples discussed herein show terminal tailed primers with 25 nucleotide tails, the two terminal tailed primers of the present invention may be constructed of various lengths appropriate for specific applications. The terminal tailed primers may also include various numbers of restriction endonuclease sites, for example, the examples herein show the presence of six such sites.

The methods of the present invention may use double-stranded DNA and may be performed in a single round that combines the benefit of maximum fidelity of a polymerase, such as T4 DNA polymerase, for mutant strand synthesis with a subsequent single high-fidelity polymerase-driven PCR step selectively for mutant strand DNA. Moreover, methods of the present invention do not require the synthesis of single-stranded DNA as a template and benefit from the ability to only use one antisense mutagenic primer for each mutation. Suitable DNA polymerases other than T4 DNA polymerase include any DNA polymerase suitable to synthesize a complementary DNA strand from single and/or double-stranded DNA, including but not limited to T7 DNA polymerase, *E.coli* DNA polymerase I and its fragments like Klenow fragment of DNA polymerase I, Moloney Murine Leukemia Virus (M-MuLV) reverse transcriptase when using single-stranded DNA as a template, or thermostable DNA polymerases and their genetically modified derivatives like Pfu DNA polymerase, Tli (Vent) DNA polymerase, Bst DNA polymerase, Taq DNA polymerase, Pwo DNA polymerase, Tth DNA polymerase, Tfl DNA polymerase, ExTaq™ DNA polymerase (a DNA polymerase blend of Taq DNA polymerase and a proofreading DNA polymerase) or similar enzymes with DNA polymerase activity. Suitable DNA ligases include T4 DNA ligase, T7 DNA ligase, Pfu DNA ligase, Taq DNA ligase, Tth DNA ligase, Tsc DNA ligase, DNA ligase (*E.coli*, NAD-dependent), and Ampligase™ Thermostable DNA ligase (NAD-dependent).

Applications for the methods of the present invention include (1) genetic engineering of genes to test their structure or function, (2) optimization of protein production when genes are tested in a model organism like yeast or *E.coli*, (3) removal/design of specific restriction enzyme cutting sites in a gene, expression vector, etc., and (4) studies on protein modification and cell signal transduction by testing/mutating glycosylation sites and phosphorylation sites of a protein.

As an example, the method of the present invention has been used to mutate simultaneously all 9 ($Hyg_{Calb}$) and 11 ($Neo_{Calb}$) CUG leucine codons (which are misread as serines in the pathogenic fungus *Candida*) of the Hyg and Neo resistance genes, respectively, to the *Candida albicans*-friendly UUG leucine codon at 100% efficiency. Furthermore, the $Hyg_{Calb}$ gene has been functionally tested and employed for targeted gene replacement in *C.albicans*.

EXAMPLES

Materials and Methods

Phosphorylation of Pooled Primers

Oligonucleotide primers were synthesized at 25-nmol scale, or 50-nmol scale for the longer anchor primers, and purified by standard desalting by the manufacturer (IDT Inc., Coralville, Iowa, USA) without further purification. Antisense mutagenic primers and the tailed 5'- and 3'-anchor primers (Table 1, below) were individually dissolved in $H_2O$ at 50 µM concentration. Subsequently, primers were pooled for simultaneous 5'-phosphorylation in a single kinase reaction by mixing 10 µL of each mutagenic primer (i.e., 7 primers for Hyg and 9 primers for Neo mutagenesis) with 3.4 µL each of the 5'- and 3'-anchor primers. 2 microliters of the pooled primers (100 pmol total oligonucleotide concentration) was phosphorylated in 25 µL of kinase buffer (70 mM Tris-HCl pH 7.6, 10 mM $MgCl_2$, 5 mM DTT, 1 mM ATP) with 5 U of T4 polynucleotide kinase (Promega) for 30 minutes at 37° C. followed by heat inactivation for 10 minutes at 70° C. and storage at −20° C. for subsequent use.

TABLE 1

Mutagenic, terminal anchor, and PCR primers used for multiple site-directed mutagenesis of the Hyg and Neo genes

| Primer | Oligonucleotide sequence | |
|---|---|---|
| Hyg-Leu15 | 5'-ACTTTTCGATCAAAAACTTCTCGAC-3' | (SEQ ID NO: 1) |
| Hyg-Leu25 | 5'-GAGAGCTGCATCAAGTCGGAGACGC-3' | (SEQ ID NO: 2) |
| Hyg-Leu48 | 5'-TATTTACCCGCAAGACATATCCACG-3' | (SEQ ID NO: 3) |
| Hyg-Leu87 | 5'-AATAGGTCAAGCTCTCGCTGAATTC-3' | (SEQ ID NO: 4) |
| Hyg-Leu103, 108, 112 | 5'-GACCGGCTGCAAAACAGCGGGCAATTCGGTTTCAGG CAAGTCTTGCAACG-3' | (SEQ ID NO: 5) |
| Hyg-Leu181 | 5'-CCCAAAGCATCAACTCATCGAGAGC-3' | (SEQ ID NO: 6) |
| Hyg-Leu205 | 5'-ATTGTCCGTCAAGACATTGTTGGAG-3' | (SEQ ID NO: 7) |
| Hyg-5'anchor-EcoRV/KpnI/HindIII | 5'-CGGTGAGTTCAGGCTTTTTCATAAGCTTGGTACCGATA TCGCTCGAC-3' | (SEQ ID NO: 8) |
| Hyg-3'anchor-BamHI/XbaI/NotI | 5'-*CTGTAGCGGCCGCTCTAGAGGATCCC*TATTCCTTTGC CCTCGGACG-3' | (SEQ ID NO: 9) |
| PCR-5'anchor-forward | 5'-GTCGAGCGATATCGGTACCAAGCTTA-3' | (SEQ ID NO: 10) |
| PCR-3'anchor-reverse | 5'-CTGTAGCGGCCGCTCTAGAGGATCC-3' | (SEQ ID NO: 11) |
| Neo-Leu39 | 5'-CCTGCGCTGACAACCGGAACACGGC-3' | (SEQ ID NO: 12) |
| Neo-Leu53, 57, 60 | 5'-CCTCGTCCTGCAATTCATTCAAGGCACCGGACAAGTC GGTCTTGAC-3' | (SEQ ID NO: 13) |
| Neo-Leu70 | 5'-CCGTCGTGGCCAACCACGATAGCCG-3' | (SEQ ID NO: 14) |
| Neo-Leu92 | 5'-CGCCCAATAGCCAACCAGTCCCTTCC-3' | (SEQ ID NO: 15) |
| Neo-Leu103 | 5'-GGTGAGATGACAAGAGATCCTGCCC-3' | (SEQ ID NO: 16) |
| Neo-Leu123 | 5'-CAAGCGTATGCAACCGCCGCATTGC-3' | (SEQ ID NO: 17) |
| Neo-Leu158 | 5'-GCTCTTCGTCCAAATCATCCTGATC-3' | (SEQ ID NO: 18) |
| Neo-Leu170 | 5'-GCCTGGCGAACAATTCGGCTGGCGC-3' | (SEQ ID NO: 19) |
| Neo-Leu212 | 5'-CCGCCACACCCAACCGGCCACAGTC-3' | (SEQ ID NO: 20) |
| Neo-5'anchor-EcoRV/KpnI/HindIII | 5'-GCAATCCATCTTGTTCAATCATAAGCTTGGTACCGATA TCGCTCGAC-3' | (SEQ ID NO: 21) |
| Neo-3'anchor-BamHI/XbaI/NotI | 5'-*CTGTAGCGGCCGCTCTAGAGGATCC*TCAGAAGAACTCG TCAAGAAGG-3' | (SEQ ID NO: 22) |

Oligonucleotide primers are in antisense orientation (except for PCR-5'anchor-forward primer) and the mutated leucine codons are underlined with the G-to-A point mutations in bold. For the anchor primers the start and stop codons are underlined and the unique 25-nucleotide tail for subsequent mutant strand-specific PCR is in italics.

Annealing of Mutagenic and Anchor Primers to Double-stranded Plasmid DNA

Double-stranded plasmid DNA of sequencing quality (QIAprep Miniprep Kit, Qiagen) was used as a template and alkaline-denatured prior to annealing of the mutagenic and anchor primers. The 1.03-kb Hyg gene (hygromycin B phosphotransferase, GenBank accession no. K01193, SEQ ID NO: 23) or the 0.80-kb Neo gene (neomycin phosphotransferase, GenBank accession no. V00618, SEQ ID NO: 24) in the Leishmania-Escherichia coli shuttle vectors pX63-Hyg or pX63-Neo served as templates, see A. Cruz, C. M. Coburn, S. M. Beverley, Double targeted gene replacement for creating null mutants, Proc. Natl. Acad. Sci. USA, 88 (1991) pp. 7170–7174, the entire contents and disclosure of which is hereby incorporated by reference. In a 20-μL reaction volume adjusted with $H_2O$, 2 μg of plasmid DNA was mixed with 2 μL of 2 M NaOH, 2 mM EDTA and incubated at room temperature for 5 minutes. Subsequently, the alkaline-denatured DNA was precipitated by adding 2 μL of 2 M ammonium acetate, pH 4.6, and 75 μL of 100% ethanol (chilled at −20° C.) followed by a 30 minute incubation at −70° C. and centrifugation in a microcentrifuge for 15 minutes. Following one wash each with 70% and 100% ethanol, the pellet was air-dried for 10 minutes and resuspended on ice in 100 μL TE buffer (10 mM Tris-HCl pH 8.0, 1 mM EDTA). For the subsequent annealing reaction adjusted to 20 μL with $H_2O$, 80 ng of a denatured plasmid DNA template (0.02 pmol) was mixed on ice with 5 μL of phosphorylated primer mixture (20 pmol total) and 2 μL of 10× annealing buffer (200 mM Tris-HCl pH 7.5, 500 mM NaCl, 100 MM $MgCl_2$). The annealing reaction was carried out in a thermal cycler by heating the mixture to 75° C. for 5 minutes followed by gradual cooling to 45° C. within 30 minutes (−1° C./minute) and to 22° C. within 12 minutes (−2° C./minute), see A. Seyfang, M. P. Kavanaugh, S. M. Landfear, Aspartate 19 and glutamate 121 are critical for transport function of the myo-inosito/$H^+$ symporter from Leishmania donovani, J. Biol. Chem., 272 (1997) pp. 24210–24215, the entire contents and disclosure of which is hereby incorporated by reference. The annealed template-primer mixture was placed on ice for subsequent assembly of mutant strand synthesis reaction.

Mutant Strand Synthesis by Primer Extension and Ligation

Mutant strand synthesis was carried out by primer extension with T4 DNA polymerase and ligation to the neighboring primer with T4 DNA ligase in a single incubation step. To the 20 μL annealed template-primer mixture from the previous step, 3 μL of 10× synthesis buffer (100 mM Tris-HCl pH 7.5, 5 mM total of dNTPs, 10 mM ATP, 20 mM DTT), 1 μL (8 U) T4 DNA polymerase (Promega), 1 μL (3 U) T4 DNA ligase (Promega) and 5 μL $H_2O$ were added on ice to give a final volume of 30 μL, followed by incubation for 2 hours at 37° C., see A. Seyfang, M. P. Kavanaugh, S. M. Landfear, Aspartate 19 and glutamate 121 are critical for transport function of the myo-inositol/$H^+$ symporter from Leishmania donovani, J. Biol. Chem., 272 (1997) pp. 24210–24215, the entire contents and disclosure of which is hereby incorporated by reference.

Amplification of Mutant Strand by High-fidelity PCR

The unique 25-nucleotide tails that flanked the 5' and 3'-terminal primers (Table 1, FIG. 1) were used as anchors for mutant strand-specific PCR amplification by a high-fidelity thermostable DNA polymerase (ExTaq™ polymerase blend, TaKaRa/Panvera, Madison, Wis., USA). In a final volume of 100 μL, 10 μL of 10×PCR buffer (100 mM Tris-HCl pH 8.3, 500 mM KCl, 20 mM $MgCl_2$), 2 μL each of 50 μM PCR 5'-anchor and PCR 3'-anchor primer (Table 1), 8 μL template of mutant strand synthesis reaction from the previous step, 200 μM each of dNTPs and 2.5 U of ExTaq™ polymerase were mixed on ice and followed by hot-start PCR. Thus, the PCR tube was transferred directly from ice to the pre-heated thermal cycler at 95° C. for an initial denaturation step of 2 minutes, followed by 25 cycles of 95° C. for 45 seconds, 55° C. for 30 seconds, 72° C. for 1 minute (Neo PCR) or 2 minutes (Hyg PCR), and finally 1 cycle of 72° C. for 10 minutes.

Generation of Candida albicans-friendly Hyg and Neo Genes and use for Targeted Gene Replacement Each PCR reaction yielded about 5 μg of amplified mutagenesis product, which was confirmed by 1.4% agarose gel electrophoresis for specificity and expected band size (FIG. 2A). Following gel extraction and purification (QIAquick gel extraction kit, Qiagen) of the 0.85-kb $Neo_{Calb}$ band and 1.08-kb $Hyg_{Calb}$ band with the mutated C.albicans-friendly leucine codons, restriction enzyme double digest of the extracted DNA at the unique HindIII and BamHI sites introduced by the 25-nucleotide tails of the terminal anchor primers was used for subsequent directional subcloning into HindIII/EcoRI/BamHI-digested pBluescript $SK^+$ vector (Stratagene). Finally, both cloned mutagenesis products were sequenced by automated sequencing to confirm the desired 9 ($Hyg_{Calb}$, SEQ ID NO: 25) and 11 ($Neo_{Calb}$, SEQ ID NO: 26) CUG-to-UUG leucine codon mutations and the absence of undesired second-site mutations.

Figure 2:
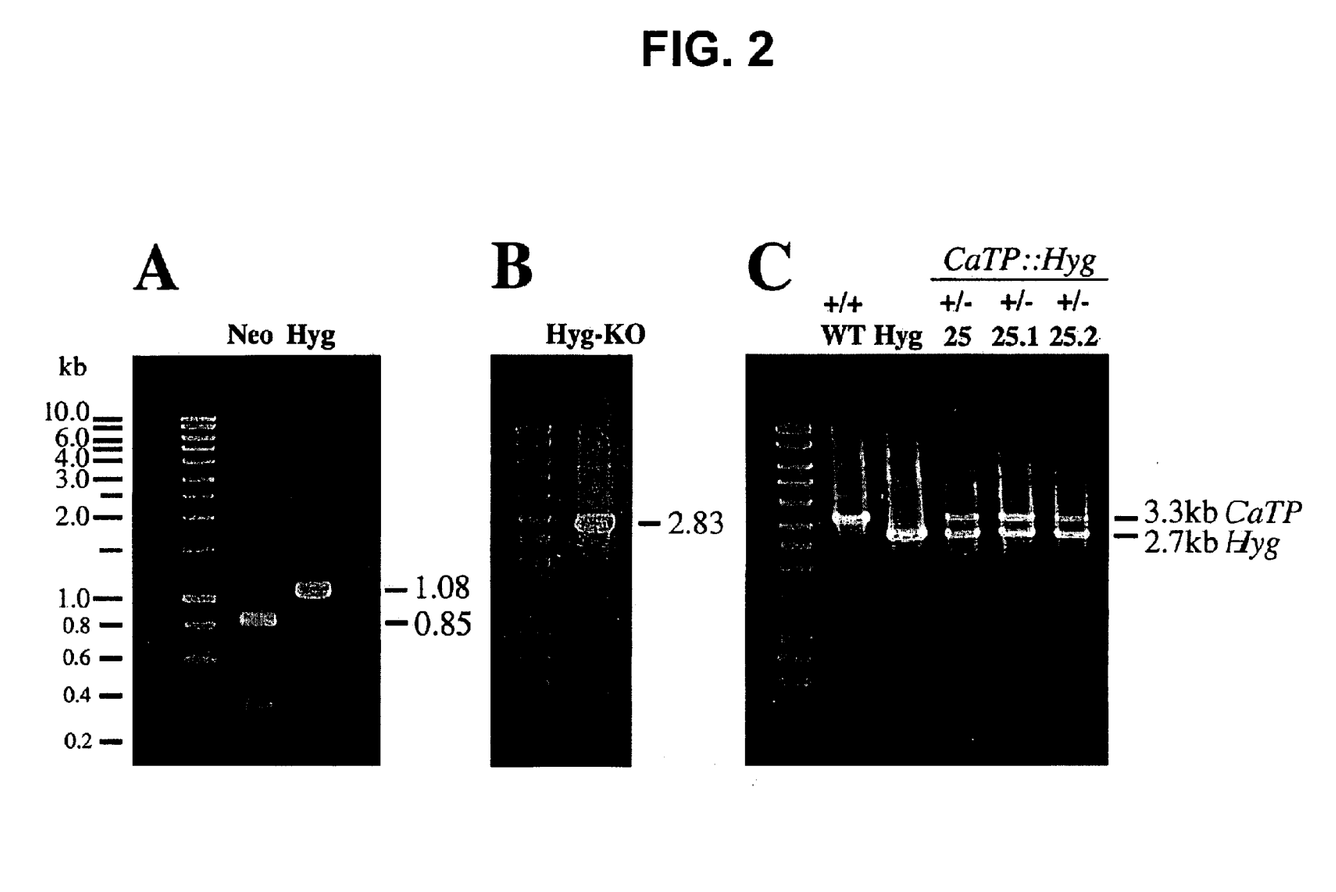

Subsequently, the C.albicans-friendly $Hyg_{Calb}$ was functionally tested and employed for targeted gene replacement of the gene for a novel C.albicans transporter protein (CaTP) of the sugar transporter superfamily (GenBank C.albicans contig6-2453:29471–27836, provided by Stanford Genome Technology Center, Stanford University, Palo Alto, Calif., USA). First, a CaTP knockout construct in pBluescript was generated by cloning an 878-bp CaTP 5'UTR fragment and a 925-bp CaTP 3'UTR fragment, respectively (both amplified by standard PCR), into the HindIII and BamHI sites that flank the 5'- and 3'-ends of $Hyg_{Calb}$ in pBluescript $SK^+$. This plasmid construct (200 ng) was used as a template to amplify the linear CaTP::$Hyg_{Calb}$ knockout construct of 2.83 kb size by PCR with ExTaq™ polymerase (1 cycle of 95° C. for 2 minutes; 30 cycles of 95° C. for 45 seconds, 53° C. for 30 seconds, 72° C. for 3 minutes; 1 cycle of 72° C. for 10 minutes) (FIG. 2, panel B). Subsequently, the PCR product was ethanol-precipitated in the presence of sodium acetate and 2 μg of CaTP::$Hyg_{Calb}$ knockout DNA was directly used for transformation of C.albicans strain SC5314 by electroporation, see J. H Jin, A. Seyfang, High-affinity myo-inositol transport in Candida albicans: Substrate specificity and pharmacology, Microbiology, 149 (2003) pp. 3371–3381, the entire contents and disclosure of which is hereby incorporated by reference. Cells were made electrocompetent by lithium acetate and DTT treatment and 40 μL of electrocompetent cells (4–8×$10^8$) was transferred to a 0.2-cm electroporation cuvette (Bio-Rad, Hercules, Calif., USA) and pulsed at 1.5 kV, 25 μF and 200 ohms in a Bio-Rad Gene Pulser, see J. R. Thompson, E. Register, J. Curotto, R. Kelly, An improved protocol for the preparation of yeast cells for transformation by electroporation, Yeast, 14 (1998) pp. 565–571; and D. M. Becker, V. Lundblad, Introduction of DNA into yeast cells, in F. M. Ausubel, R. Brent, R. E. Kingston, D. D. Moore, J. G. Seidman, J. A. Smith, K. Struhl, (Eds.), Short Protocols in Molecular Biology, John Wiley & Sons, New York, 1999, pp. 13.31–13.36, the entire contents and disclosures of which are hereby incorporated by reference. Candida cells transformed with CaTP::Hyg$_{Calb}$ knockout DNA or mock-transformed without DNA as a control were plated on YPD agar plates containing 500 μg/mL hygromycin B (Calbiochem) and incubated at 30° C. Single colonies were picked after 3 to 5 days, grown for two days in 2 mL of YPD medium (1% yeast extract, 2% peptone, 2% glucose; Bio101, Vista, Calif., USA) with 250 μg/mL hygromycin B at 200 rpm, and subsequently used for purification of genomic DNA by a 'miniprep' method with acid-washed glass beads (425–600 μm, Sigma) and TELT buffer (50 mM Tris-HCl pH 8.0, 63 mM EDTA, 2.5 M LiCl, 4% Triton X-100), see E. Medina-Acosta, G. A. Cross, Rapid isolation of DNA from trypanosomatid protozoa using a simple 'mini-prep' procedure, Mol. Biochem. Parasitol., 59 (1993) pp. 327–329, the entire contents and disclosure of which is hereby incorporated by reference. Finally, heterozygous CaTP::Hyg$_{Calb}$ knockout cells were confirmed by PCR using 150 ng of genomic miniprep DNA in 50 μL reaction volume (1 cycle of 95° C. for 2 minutes; 35 cycles of 95° C. for 45 seconds, 53° C. for 30 seconds, 72° C. for 2.5 minutes; 1 cycle of 72° C. for 10 minutes)(FIG. 2, panel C).

Results

Oligonucleotide-directed site-specific mutagenesis is greatly affected by the design of mutagenic oligonucleotide primers and the quality of subsequent primer-template annealing, two aspects which become even more important in multiple-site mutagenesis. For optimal annealing and subsequent initiation of polymerase synthesis according to the present invention, mutagenic primers were designed to have a G or C at their 3' ends where DNA synthesis would start, with the mutation in the center of the oligonucleotide primer (Table 1). In these examples, primers had a length of 25 nucleotides, unless three close mutations were combined in one larger mutagenic primer, and were of standard commercial quality without additional purification steps. For the terminal, tailed anchor primers, the unique 25-nucleotide tail for subsequent mutant strand-specific PCR contained three restriction endonuclease sites each (Table 1) to allow convenient subcloning of the PCR product into different vectors. All primers were 5'-phosphorylated for optimum ligation of the nicks between the 3' end of the newly synthesized DNA strand and the 5' end of the following primer. To facilitate this step, the kinase reaction was performed in a single tube with the pooled primers combined. Furthermore, in embodiments of the present invention, methods are employed that utilize a three-fold molar excess of mutagenic primers over the terminal anchor primers, which significantly contribute to the high efficiency of this method by guaranteeing that the final PCR step would amplify mutant strands with all mutagenic primers annealed and incorporated.

Most mutagenesis protocols require either two complementary primers for each introduced mutation if they are PCR-based protocols, or, in the case of non-PCR-based methods, call for the synthesis of single-stranded template DNA or the preparation of uracil containing template DNA as additional steps, see T. A. Kunkel, Rapid and efficient site-specific mutagenesis without phenotype selection, Proc. Natl. Acad. Sci. USA, 82 (1985) pp. 488–492; M. P. Weiner, G. L. Costa, W. Schoettlin, J. Cline, E. Mathur, J. C. Bauer, Site-directed mutagenesis of double-stranded DNA by the polymerase chain reaction, Gene, 151 (1994) pp. 119–123; T. M. Ishii, P. Zerr, X. M. Xia, C. T. Bond, J. Maylie, J. P. Adelman, Site-directed mutagenesis, Methods Enzymol., 293 (1998) pp. 53–71; I. Michaelian, A. Sergeant, A general and fast method to generate multiple site directed mutations, Nucleic Acids Res., 20 (1992) p. 376; Y. G. Kim, S. Maas, Multiple site mutagenesis with high targeting efficiency in one cloning step, Biotechniques, 28 (2000) pp. 196–198; G. C. Lee, L. C. Lee, V. Sava, J. F. Shaw, Multiple mutagenesis of non-universal serine codons of the Candida rugosa LIP2 gene and biochemical characterization of purified recombinant LIP2 lipase overexpressed in Pichia pastoris, Biochem. J., 366 (2002) pp. 603–611; and A. Seyfang, M. P. Kavanaugh, S. M. Landfear, Aspartate 19 and glutamate 121 are critical for transport function of the myo-inositol/H$^+$ symporter from Leishmania donovani, J. Biol. Chem., 272 (1997) pp. 24210–24215, the entire contents and disclosures of which are hereby incorporated by reference. The methods of the present invention combine the benefit of only one antisense primer per mutation with the convenience of using double-stranded plasmid DNA as a template. These benefits were enabled by using alkaline denaturing of double-stranded DNA for 5 minutes followed by resuspension of the DNA pellet in annealing buffer on ice to minimize the reannealing of double-stranded template DNA prior to the addition of primers. Furthermore, in embodiments, methods of the present invention use a hot-start method for primer-template annealing: the annealing reaction is assembled on ice and directly transferred to a preheated thermal cycler at 75° C. for subsequent gradual and efficient primer-template annealing over 30 to 40 minutes.

An overview of a multiple-site mutagenesis protocol according to an embodiment of the present invention is given in the schematic diagram of FIG. 1. Mutant strand synthesis was carried out by primer extension and ligation in a single incubation step and took advantage of the maximum fidelity of a polymerase such as T4 DNA polymerase, compared to thermostable polymerases and PCR cycling, see T. A. Kunkel, L. A. Loeb, M. F. Goodman, On the fidelity of DNA replication: The accuracy of T4 DNA polymerase in copying phi X174 DNA in vitro, J. Biol. Chem., 259 (1984) pp. 1539–1545; K. R. Tindall, T. A. Kunkel, Fidelity of DNA synthesis by the Thermus aquaticus DNA polymerase, Biochemistry, 27 (1988) pp. 6008–6013; and J. Cline, J. C. Braman, H. H. Hogrefe, PCR Fidelity of Pfu DNA polymerase and other thermostable DNA polymerases, Nucleic Acids Res., 24 (1996) pp. 3546–3551, the entire contents and disclosures of which are hereby incorporated by reference. Subsequently, amplification of full-length mutant strands was performed by high-fidelity polymerase-driven PCR, which used the unique mutant strand-specific tails introduced by the two terminal anchor primers (FIG. 1). In particular embodiments, the methods of the present invention utilize ExTaq™ polymerase as an enzyme blend with high proofreading capacity, since it combines high-fidelity thermostable polymerase activity with a superb product yield equal or higher than that of Taq polymerase, even for challenging genes with high GC content as found in the protozoan flagellate Leishmania, see A. Seyfang, M. P. Kavanaugh, S. M. Landfear, Aspartate 19 and glutamate 121 are critical for transport function of the myo-inositol/H$^+$ symporter from Leishmania donovani, J. Biol. Chem., 272 (1997) pp. 24210–24215, the entire contents and disclosure of which is hereby incorporated by reference. However, it should be noted that Taq polymerase and other suitable polymerases may be used according to the methods of the present invention in light of the teachings contained herein. Hence the final PCR step yielded about 5 μg of amplified mutagenesis product from approximately 10 ng of mutant strand DNA (8 μL) as a template (FIG. 2, panel A). Subsequent directional subcloning of the PCR products into the vector pBluescript was facilitated by the choice of six different restriction endonuclease sites introduced by the two terminal anchor primers (Table 1). Automated sequencing of both cloned mutagenesis products $Hyg_{Calb}$ and $Neo_{Calb}$ in pBluescript confirmed that all 9 and 11 simultaneously generated site-directed mutations, respectively, had been introduced into the two resistance genes at a 100% efficiency rate, and no undesired second-site mutations were observed.

Furthermore, the $Hyg_{Calb}$ gene was functionally tested and used for targeted gene replacement of a novel transporter gene in C.albicans that codes for a putative transport protein (CaTP) of the sugar transporter superfamily, which shows homology to fructose/$H^+$ and myo-inositol/$H^+$ permeases of lower eukaryotes. C.albicans has a non-universal codon usage for the amino acid serine whereby the universal leucine codon CUG is translated as serine in this pathogenic fungus, M. A. Santos, V. M. Perreau, M. F. Tuite, Transfer RNA structural change is a key element in the reassignment of the CUG codon in Candida albicans, EMBO J., 15 (1996) pp. 5060–5068, the entire contents and disclosure of which is hereby incorporated by reference. Hence the need to engineer the two Candida-friendly dominant selection markers, which would allow genetic manipulation of C.albicans without the need for different auxotrophic strains. In the present invention, the effective inhibitory concentrations of hygromycin B (Calbiochem; $IC_{50}$=9 µg/ml, $IC_{90}$=31 µg/ml) and of the neomycin analogue G418 (Gibco-BRL; $IC_{50}$=11 µg/ml, $IC_{90}$=39 µg/ml) for C.albicans cells grown in YPD medium at 30° C. were determined, see J. H Jin, A. Seyfang, High-affinity myo-inositol transport in Candida albicans: Substrate specificity and pharmacology, Microbiology, 149 (2003) pp. 3371–3381, the entire contents and disclosure of which is hereby incorporated by reference. To generate heterozygous CaTP knockout cells, $Hyg_{Calb}$ was used in pBluescript to generate a CaTP::$Hyg_{Calb}$ knockout construct by subcloning an 878-bp 5'UTR and 925-bp 3'UTR fragment of the untranslated CaTP flanking regions immediately upstream and downstream of the $Hyg_{Calb}$ resistance marker. Following PCR amplification of the linear 2.83-kb knockout construct from this plasmid construct (FIG. 2, panel B), Candida cells were transformed by electroporation with 2 µg of CaTP::$Hyg_{Calb}$ knockout DNA and transformants were selected on YPD agar plates at 500 µg/mL hygromycin concentration. From these plates, 15 single colonies were randomly picked and grown in liquid culture at 250 µg/mL hygromycin concentration for isolation of genomic DNA. Following PCR analysis, three separate heterozygous CaTP::$Hyg_{Calb}$ knockout clones were confirmed and one of these clones (clone 25) was further recloned through an additional round of streaking out single colonies on YPD agar plates at 500 µg/mL hygromycin concentration. A band of 3.3 kb for CaTP and 2.7 kb for $Hyg_{Calb}$ was consistent with a heterozygous $CaTP^{+/hyg}$ genotype (clone 25 and subclones 25.1 and 25.2 in FIG. 2, panel C), which was further confirmed by subsequent Southern blot analysis (data not shown). Hence these data demonstrate the feasibility of engineering whole genes with an altered codon usage for heterologous expression by generating more than 10 mutations simultaneously with this rapid and efficient multiple-site mutagenesis protocol.

Discussion

The present invention provides for a rapid and simple multiple site-directed mutagenesis method, which has the advantage of using double-stranded DNA as a template and does not require cloning of the gene into a specific mutagenesis vector prior to site-directed mutagenesis. Hence the template DNA may be a gene in any vector, including DNA from a cDNA library, or single-stranded DNA directly derived from isolated mRNA after reverse transcriptase reaction and first-strand cDNA synthesis. Furthermore, this method requires only one antisense oligonucleotide mutagenic primer per mutation, while many other protocols call for two complementary mutagenic primers per mutation, see M. P. Weiner, G. L. Costa, W. Schoettlin, J. Cline, E. Mathur, J. C. Bauer, Site-directed mutagenesis of double-stranded DNA by the polymerase chain reaction, Gene, 151 (1994) pp. 119–123; I. Michaelian, A. Sergeant, A general and fast method to generate multiple site directed mutations, Nucleic Acids Res., 20 (1992) p. 376; Y. G. Kim, S. Maas, Multiple site mutagenesis with high targeting efficiency in one cloning step, Biotechniques, 28 (2000) pp. 196–198; and G. C. Lee, L. C. Lee, V. Sava, J. F. Shaw, Multiple mutagenesis of non-universal serine codons of the Candida rugosa LIP2 gene and biochemical characterization of purified recombinant LIP2 lipase overexpressed in Pichia pastoris, Biochem. J., 366 (2002) pp. 603–611, the entire contents and disclosures of which are hereby incorporated by reference. The most significant advantage of this protocol is that more than 10 mutations may be generated simultaneously in a single round that incorporates all mutations during one round of mutant strand synthesis with a polymerase such as T4 DNA polymerase and ligase, and only one round of high-fidelity PCR is needed to amplify the mutant strand specifically and selectively with the unique nucleotide tails introduced by the terminal anchor primers (FIG. 1).

For the mutagenesis reaction, in particular embodiments, the present invention provides a stoichiometry of approximately 100:1 for the ratio of each mutagenic oligonucleotide primer to template DNA and 33:1 for the ratio of each of the two terminal PCR anchor primers to template DNA (Hyg: 2.6 pmol or Neo: 2.1 pmol of each mutagenic primer with 0.02 pmol template DNA). Thus the high efficiency of this method of up to 100% benefits from (i) a threefold molar excess of mutagenic primer over terminal anchor primer, which ensures incorporation of all mutations in the amplified mutant strand, and (ii) a hot-start annealing procedure that guarantees equal and specific annealing of all primers during a gradual, standardized primer-template annealing step of 30 to 40 minutes.

Mutant strand synthesis was performed by T4 DNA polymerase, which lacks any detectable strand displacement or 5'→3' exonuclease activities and has the lowest error rate of all commercially available DNA polymerases, T. A. Kunkel, L. A. Loeb, M. F. Goodman, On the fidelity of DNA replication: The accuracy of T4 DNA polymerase in copying phi X174 DNA in vitro, J. Biol. Chem., 259 (1984) pp. 1539–1545, the entire contents and disclosure of which is hereby incorporated by reference. Hence mutagenic primers were not at risk to loose their point mutation by displacement from their 5' end with the mutant strand originating from a neighboring primer upstream. In contrast, thermostable high-fidelity DNA polymerases like Pfu or Tli (Vent) DNA polymerase contain strand displacement activity and would be less suited for mutant strand synthesis with multiple mutagenic primers simultaneously, H. Kong, R. B. Kucera, W. E. Jack, Characterization of a DNA polymerase from the hyperthermophile archaea Thermococcus litoralis: Vent DNA polymerase, steady state kinetics, thermal stability, processivity, strand displacement, and exonuclease activities, J. Biol. Chem., 268 (1993) pp. 1965–1975, the entire contents and disclosure of which is hereby incorporated by reference. Other DNA polymerases may be used in the methods of the present invention, but should possess low error rates if larger genes or DNA sequences are to be mutated, to reduce the chances of introducing unwanted second-site mutations. The distance between neighboring primers had no noticeable effect on the efficiency of this mutagenesis protocol with a combined DNA polymerase/ligase reaction step for mutant strand synthesis, and gaps between neighboring primers ranged from 6 to 381 bases for $Hyg_{Calb}$ and from 5 to 127 bases for $Neo_{Calb}$ mutagenesis, respectively.

The methods of the present invention provide for many benefits identified herein, including the use of double-stranded plasmid DNA as template DNA in any vector or cDNA library, without the need to synthesize single-stranded or uracil-containing template DNA first, nor the need to subclone the gene in a special mutagenesis vector prior to site-directed mutagenesis. Furthermore, only one set of anti-sense mutagenic primers is required, in contrast to a pair of two complementary primers for each mutation in most solely PCR-based mutagenesis protocols.

Site-directed mutagenesis has become a gold standard to probe the structure-function relationship of proteins or nucleic acids, and for utilization in genetic engineering. Potential applications for the multiple site-directed mutagenesis methods of the present invention range from codon optimization for heterologous expression to genetic engineering of whole genes, see G. C. Lee, L. C. Lee, V. Sava, J. F. Shaw, Multiple mutagenesis of non-universal serine codons of the Candida rugosa LIP2 gene and biochemical characterization of purified recombinant LIP2 lipase overexpressed in Pichia pastoris, Biochem. J., 366 (2002) pp. 603–611; and N. R. Cohen, D. A. Knecht, H. F. Lodish, Functional expression of rat GLUT1 glucose transporter in Dictyostelium discoideum, Biochem. J., 315 (1996) pp. 971–975, the entire contents and disclosures of which are hereby incorporated by reference. This includes the design of cysteine-less proteins for subsequent cysteine-scanning or disulfide-scanning mutagenesis and employment of amino acid-specific chemistry in engineered genes, see J. A. Javitch, L. Shi, G. Liapakis, Use of the substituted cysteine accessibility method to study the structure and function of G protein-coupled receptors, Methods Enzymol., 343 (2002) pp. 137–156; and M. A. Danielson, R. B. Bass, J. J. Falke, Cysteine and disulfide scanning reveals a regulatory alpha-helix in the cytoplasmic domain of the aspartate receptor, J. Biol. Chem., 272 (1997) pp. 32878–32888, the entire contents and disclosures of which are hereby incorporated by reference. Another application is the removal of all undesired and simultaneous design of novel restriction endonuclease sites in one step for generation of new cloning and expression vectors or optimization of genes for selectable markers. Similarly, removal of multiple potential phosphorylation sites or N-linked glycosylation sites in studies that probe the functional regulation and post-translational modificaton of proteins has been cumbersome and used to require several rounds of site-directed mutagenesis, whereas the methods of the present invention would allow performance of the necessary mutations simultaneously in a single round. Other examples include the introduction of dominant selection markers into organisms with a strong codon bias, like the malaria parasite Plasmodium falciparum with its AT-rich codon bias, or into microbial pathogens with a non-universal codon usage like the opportunistic fungus C.albicans. The lower eukaryote Dictyostelium discoideum is an attractive heterologous expression system and functional expression of the mammalian glucose transporter GLUT1 in D.discoideum was possible after codon optimization of the first 11 amino acids for the AT-rich codon bias of this microorganism, see N. R. Cohen, D. A. Knecht, H. F. Lodish, Functional expression of rat GLUT1 glucose transporter in Dictyostelium discoideum, Biochem. J., 315 (1996) pp. 971–975. Thus these diverse examples illustrate that the user-friendly and rapid methods of the present invention for multiple site-directed mutagenesis should find a wide and diverse range of applications.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for site-directed mutagenesis comprising the steps of:
   providing two terminal tailed primers comprising an anchor portion and a portion having nucleotide sequences respectively complementary to each end of a gene to be mutated;
   annealing the complementary portion of said terminal tailed primers and a set of mutagenic primers to template DNA in a single step;
   synthesizing a mutant strand by primer extension and ligation; and
   amplifying said mutant strand by polymerase chain reaction.

2. The method of claim 1, wherein said method is used to mutate 5 nucleotides simultaneously.

3. The method of claim 1, wherein said method is used to mutate 10 nucleotides simultaneously.

4. The method of claim 1, wherein said method is used to mutate more than 10 nucleotides simultaneously.

5. The method of claim 1, wherein said method is used to mutate 20 nucleotides simultaneously.

6. The method of claim 1, wherein said method is used to mutate 30 nucleotides simultaneously.

7. The method of claim 1, wherein said method is used to mutate 40 nucleotides simultaneously.

8. The method of claim 1, wherein said method is used to mutate 50 nucleotides simultaneously.

9. The method of claim 1, wherein said method is used to mutate more than 50 nucleotides simultaneously.

10. The method of claim 1, wherein said complementary nucleotide sequences of said terminal tailed primers are 25 nucleotides in length.

11. The method of claim 1, wherein said complementary nucleotide sequences of said terminal tailed primers are less than 25 nucleotides in length.

12. The method of claim 1, wherein said complementary nucleotide sequences of said terminal tailed primers are more than 25 nucleotides in length.

13. The method of claim 1, wherein each said anchor portion of said terminal tailed primers comprise at least one restriction endonuclease site.

14. The method of claim 1, wherein each said anchor portion of said terminal tailed primers comprise at least three restriction endonuclease sites.

15. The method of claim 1, wherein said set of mutagenic primers comprises one mutagenic primer for each desired mutation.

16. The method of claim 1, wherein said set of mutagenic primers comprises one mutagenic primer for two or more desired mutations.

17. The method of claim 1, wherein said two or more desired mutations are located less than 25 nucleotides apart.

18. The method of claim 1, wherein said primer extension is performed using a DNA polymerase.

19. The method of claim 18, wherein said DNA polymerase comprises T4 DNA polymerase.

20. The method of claim 18, wherein said DNA polymerase comprises T7 DNA polymerase.

21. The method of claim 18, wherein said DNA polymerase comprises *E.coli* DNA polymerase I.

22. The method of claim 18, wherein said DNA polymerase comprises the Klenow fragment of DNA polymerase I.

23. The method of claim 18, wherein said DNA polymerase comprises Moloney Murine Leukemia Virus reverse transcriptase.

24. The method of claim 18, wherein said DNA polymerase comprises Pfu DNA polymerase.

25. The method of claim 18, wherein said DNA polymerase comprises Tli DNA polymerase.

26. The method of claim 18, wherein said DNA polymerase comprises Bst DNA polymerase.

27. The method of claim 18, wherein said DNA polymerase comprises Taq DNA polymerase.

28. The method of claim 18, wherein said DNA polymerase comprises Pwo DNA polymerase.

29. The method of claim 18, wherein said DNA polymerase comprises Tth DNA polymerase.

30. The method of claim 18, wherein said DNA polymerase comprises Tfl DNA polymerase.

31. The method of claim 1, wherein said ligation is performed using a DNA ligase.

32. The method of claim 31, wherein said ligase comprises T4 DNA ligase.

33. The method of claim 31, wherein said ligase comprises T7 DNA ligase.

34. The method of claim 31, wherein said ligase comprises Pfu DNA ligase.

35. The method of claim 31, wherein said ligase comprises Tth DNA ligase.

36. The method of claim 31, wherein said ligase comprises Tsc DNA ligase.

37. The method of claim 31, wherein said ligase comprises Taq DNA ligase.

38. The method of claim 31, wherein said ligase comprises an NAD-dependent DNA ligase.

39. The method of claim 1, wherein said polymerase chain reaction is performed using a DNA polymerase.

40. The method of claim 39, wherein said DNA polymerase comprises Pfu DNA polymerase.

41. The method of claim 39, wherein said DNA polymerase comprises Pwo DNA polymerase.

42. The method of claim 39, wherein said DNA polymerase comprises Tli DNA polymerase.

43. The method of claim 39, wherein said DNA polymerase comprises Tth DNA polymerase.

44. The method of claim 39, wherein said DNA polymerase comprises Tfl DNA polymerase.

45. The method of claim 1, wherein said polymerase chain reaction is performed using a DNA polymerase blend comprising at least two DNA polymerases.

46. The method of claim 45, wherein said DNA polymerase blend comprises Taq DNA polymerase and a proofreading DNA polymerase.

47. The method of claim 1, wherein said template DNA is double-stranded DNA.

48. The method of claim 1, wherein said template DNA is single-stranded DNA.

49. The method of claim 1, wherein said mutagenic primers comprise a three-fold molar excess over said terminal tailed primers.

50. The method of claim 1, wherein said mutagenic primers each have a G or C at their 3' ends at the location at which DNA synthesis is initiated.

51. The method of claim 1, wherein said mutagenic primers are 5'-phosphorylated.

52. The method of claim 1, wherein said terminal tailed primers are 5'-phosphorylated.

* * * * *

SEQUENCE LISTING

<160> NUMBER OF SEQ ID NOS: 26

<210> SEQ ID NO 1
<211> LENGTH: 25
<212> TYPE: DNA
<213> ORGANISM: Artificial
<220> FEATURE:
<223> OTHER INFORMATION: Oligonucleotide primer

<400> SEQUENCE: 1
acttttcgat caaaaacttc tcgac                                         25

<210> SEQ ID NO 2
<211> LENGTH: 25
<212> TYPE: DNA
<213> ORGANISM: Artificial
<220> FEATURE:
<223> OTHER INFORMATION: Oligonucleotide primer

<400> SEQUENCE: 2

-continued gagagctgca tcaagtcgga gacgc                                         25

<210> SEQ ID NO 3
<211> LENGTH: 25
<212> TYPE: DNA
<213> ORGANISM: Artificial
<220> FEATURE:
<223> OTHER INFORMATION: Oligonucleotide primer

<400> SEQUENCE: 3
tatttacccg caagacatat ccacg                                         25

<210> SEQ ID NO 4
<211> LENGTH: 25
<212> TYPE: DNA
<213> ORGANISM: Artificial
<220> FEATURE:
<223> OTHER INFORMATION: Oligonucleotide primer

<400> SEQUENCE: 4
aataggtcaa gctctcgctg aattc                                         25

<210> SEQ ID NO 5
<211> LENGTH: 50
<212> TYPE: DNA
<213> ORGANISM: Artificial
<220> FEATURE:
<223> OTHER INFORMATION: Oligonucleotide primer

<400> SEQUENCE: 5
gaccggctgc aaaacagcgg gcaattcggt ttcaggcaag tcttgcaacg              50

<210> SEQ ID NO 6
<211> LENGTH: 25
<212> TYPE: DNA
<213> ORGANISM: Artificial
<220> FEATURE:
<223> OTHER INFORMATION: Oligonucleotide primer

<400> SEQUENCE: 6
cccaaagcat caactcatcg agagc                                         25

<210> SEQ ID NO 7
<211> LENGTH: 25
<212> TYPE: DNA
<213> ORGANISM: Artificial
<220> FEATURE:
<223> OTHER INFORMATION: Oligonucleotide primer

<400> SEQUENCE: 7
attgtccgtc aagacattgt tggag                                         25

<210> SEQ ID NO 8
<211> LENGTH: 47
<212> TYPE: DNA
<213> ORGANISM: Artificial
<220> FEATURE:
<223> OTHER INFORMATION: Oligonucleotide primer

<400> SEQUENCE: 8
cggtgagttc aggcttttc ataagcttgg taccgatatc gctcgac                  47

<210> SEQ ID NO 9
<211> LENGTH: 46
<212> TYPE: DNA

-continued

```
<213> ORGANISM: Artificial
<220> FEATURE:
<223> OTHER INFORMATION: Oligonucleotide primer

<400> SEQUENCE: 9
ctgtagcggc cgctctagag gatccctatt cctttgccct cggacg         46

<210> SEQ ID NO 10
<211> LENGTH: 26
<212> TYPE: DNA
<213> ORGANISM: Artificial
<220> FEATURE:
<223> OTHER INFORMATION: Oligonucleotide primer

<400> SEQUENCE: 10
gtcgagcgat atcggtacca agctta                               26

<210> SEQ ID NO 11
<211> LENGTH: 25
<212> TYPE: DNA
<213> ORGANISM: Artificial
<220> FEATURE:
<223> OTHER INFORMATION: Oligonucleotide primer

<400> SEQUENCE: 11
ctgtagcggc cgctctagag gatcc                                25

<210> SEQ ID NO 12
<211> LENGTH: 25
<212> TYPE: DNA
<213> ORGANISM: Artificial
<220> FEATURE:
<223> OTHER INFORMATION: Oligonucleotide primer

<400> SEQUENCE: 12
cctgcgctga caaccggaac acggc                                25

<210> SEQ ID NO 13
<211> LENGTH: 46
<212> TYPE: DNA
<213> ORGANISM: Artificial
<220> FEATURE:
<223> OTHER INFORMATION: Oligonucleotide primer

<400> SEQUENCE: 13
cctcgtcctg caattcattc aaggcaccgg acaagtcggt cttgac         46

<210> SEQ ID NO 14
<211> LENGTH: 25
<212> TYPE: DNA
<213> ORGANISM: Artificial
<220> FEATURE:
<223> OTHER INFORMATION: Oligonucleotide primer

<400> SEQUENCE: 14
ccgtcgtggc caaccacgat agccg                                25

<210> SEQ ID NO 15
<211> LENGTH: 25
<212> TYPE: DNA
<213> ORGANISM: Artificial
<220> FEATURE:
<223> OTHER INFORMATION: Oligonucleotide primer

<400> SEQUENCE: 15
cgcccaatag caaccagtcc cttcc                                25
```

```
<210> SEQ ID NO 16
<211> LENGTH: 25
<212> TYPE: DNA
<213> ORGANISM: Artificial
<220> FEATURE:
<223> OTHER INFORMATION: Oligonucleotide primer

<400> SEQUENCE: 16
ggtgagatga caagagatcc tgccc                                    25

<210> SEQ ID NO 17
<211> LENGTH: 25
<212> TYPE: DNA
<213> ORGANISM: Artificial
<220> FEATURE:
<223> OTHER INFORMATION: Oligonucleotide primer

<400> SEQUENCE: 17
caagcgtatg caaccgccgc attgc                                    25

<210> SEQ ID NO 18
<211> LENGTH: 25
<212> TYPE: DNA
<213> ORGANISM: Artificial
<220> FEATURE:
<223> OTHER INFORMATION: Oligonucleotide primer

<400> SEQUENCE: 18
gctcttcgtc caaatcatcc tgatc                                    25

<210> SEQ ID NO 19
<211> LENGTH: 25
<212> TYPE: DNA
<213> ORGANISM: Artificial
<220> FEATURE:
<223> OTHER INFORMATION: Oligonucleotide primer

<400> SEQUENCE: 19
gcctggcgaa caattcggct ggcgc                                    25

<210> SEQ ID NO 20
<211> LENGTH: 25
<212> TYPE: DNA
<213> ORGANISM: Artificial
<220> FEATURE:
<223> OTHER INFORMATION: Oligonucleotide primer

<400> SEQUENCE: 20
ccgccacacc caaccggcca cagtc                                    25

<210> SEQ ID NO 21
<211> LENGTH: 47
<212> TYPE: DNA
<213> ORGANISM: Artificial
<220> FEATURE:
<223> OTHER INFORMATION: Oligonucleotide primer

<400> SEQUENCE: 21
gcaatccatc ttgttcaatc ataagcttgg taccgatatc gctcgac            47

<210> SEQ ID NO 22
<211> LENGTH: 47
<212> TYPE: DNA
<213> ORGANISM: Artificial
<220> FEATURE:
```

<223> OTHER INFORMATION: Oligonucleotide primer

<400> SEQUENCE: 22

```
ctgtagcggc cgctctagag gatcctcaga agaactcgtc aagaagg        47
```

<210> SEQ ID NO 23
<211> LENGTH: 1026
<212> TYPE: DNA
<213> ORGANISM: Streptomyces hygroscopicus

<400> SEQUENCE: 23

```
atgaaaaagc ctgaactcac cgcgacgtct gtcgagaagt ttctgatcga aaagttcgac     60
agcgtctccg acctgatgca gctctcggag gcgaagaat ctcgtgcttt cagcttcgat    120
gtaggagggc gtggatatgt cctgcgggta aatagctgcg ccgatggttt ctacaaagat   180
cgttatgttt atcggcactt tgcatcggcc gcgctcccga ttccggaagt gcttgacatt   240
ggggaattca gcgagagcct gacctattgc atctcccgcc gtgcacaggg tgtcacgttg   300
caagacctgc ctgaaaccga actgcccgct gttctgcagc cggtcgcgga ggccatggat   360
gcgatcgctg cggccgatct tagccagacg agcgggttcg cccattcgg accgcaagga   420
atcggtcaat acactacatg gcgtgatttc atatgcgcga ttgctgatcc ccatgtgtat   480
cactggcaaa ctgtgatgga cgacaccgtc agtgcgtccg tcgcgcaggc tctcgatgag   540
ctgatgcttt gggccgagga ctgccccgaa gtccggcacc tcgtgcacgc ggatttcggc   600
tccaacaatg tcctgacgga caatggccgc ataacagcgg tcattgactg gagcgaggcg   660
atgttcgggg attcccaata cgaggtcgcc aacatcttct tctggaggcc gtggttggct   720
tgtatggagc agcagacgcg ctacttcgag cggaggcatc cggagcttgc aggatcgccg   780
cggctccggg cgtatatgct ccgcattggt cttgaccaac tctatcagag cttggttgac   840
ggcaatttcg atgatgcagc ttgggcgcag ggtcgatgcg acgcaatcgt ccgatccgga   900
gccgggactg tcgggcgtac acaaatcgcc cgcagaagcg cggccgtctg gaccgatggc   960
tgtgtagaag tactcgccga tagtggaaac cgacgcccca gcactcgtcc gagggcaaag  1020
gaatag                                                              1026
```

<210> SEQ ID NO 24
<211> LENGTH: 795
<212> TYPE: DNA
<213> ORGANISM: Streptomyces fradiae

<400> SEQUENCE: 24

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcagggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag   300
gatctcctgt catctcacct tgctcctgcc gagaaagtat ccatcatggc tgatgcaatg   360
cggcggctgc atacgcttga tccggctacc tgcccattcg accaccaagc gaaacatcgc   420
atcgagcgag cacgtactcg gatggaagcc ggtcttgtcg atcaggatga tctggacgaa   480
gagcatcagg ggctcgcgcc agccgaactg ttcgccaggc tcaaggcgcg catgcccgac   540
ggcgaggatc tcgtcgtgac ccatggcgat gcctgcttgc cgaatatcat ggtggaaaat   600
ggccgctttt ctggattcat cgactgtggc cggctgggtg tggcggaccg ctatcaggac   660
```

```
atagcgttgg ctacccgtga tattgctgaa gagcttggcg gcgaatgggc tgaccgcttc      720
ctcgtgcttt acggtatcgc cgctcccgat tcgcagcgca tcgccttcta tcgccttctt      780
gacgagttct tctga                                                       795

<210> SEQ ID NO 25
<211> LENGTH: 1026
<212> TYPE: DNA
<213> ORGANISM: Artificial
<220> FEATURE:
<223> OTHER INFORMATION: mutated Hygromycin B phosphotransferase gene

<400> SEQUENCE: 25
atgaaaaagc ctgaactcac cgcgacgtct gtcgagaagt ttttgatcga aaagttcgac       60
agcgtctccg acttgatgca gctctcggag ggcgaagaat ctcgtgcttt cagcttcgat      120
gtaggagggc gtggatatgt cttgcgggta aatagctgcg ccgatggttt ctacaaagat      180
cgttatgttt atcggcactt tgcatcggcc gcgctcccga ttccggaagt gcttgacatt      240
ggggaattca gcgagagcct gacctattgc atctcccgcc gtgcacaggg tgtcacgttg      300
caagacttgc ctgaaaccga attgcccgct gttttgcagc cggtcgcgga ggccatggat      360
gcgatcgctg cggccgatct tagccagacg agcgggttcg gcccattcgg accgcaagga      420
atcggtcaat acactacatg gcgtgatttc atatgcgcga ttgctgatcc ccatgtgtat      480
cactggcaaa ctgtgatgga cgacaccgtc agtgcgtccg tcgcgcaggc tctcgatgag      540
ttgatgcttt gggccgagga ctgccccgaa gtccggcacc tcgtgcacgc ggatttcggc      600
tccaacaatg tcttgacgga caatggccgc ataacagcgg tcattgactg gagcgaggcg      660
atgttcgggg attcccaata cgaggtcgcc aacatcttct tctggaggcc gtggttggct      720
tgtatggagc agcagacgcg ctacttcgag cggaggcatc cggagcttgc aggatcgccg      780
cggctccggg cgtatatgct ccgcattggt cttgaccaac tctatcagag cttggttgac      840
ggcaatttcg atgatgcagc ttgggcgcag ggtcgatgcg acgcaatcgt ccgatccgga      900
gccgggactg tcgggcgtac acaaatcgcc cgcagaagcg cggccgtctg gaccgatggc      960
tgtgtagaag tactcgccga tagtggaaac cgacgcccca gcactcgtcc gagggcaaag     1020
gaatag                                                                1026

<210> SEQ ID NO 26
<211> LENGTH: 795
<212> TYPE: DNA
<213> ORGANISM: Artificial
<220> FEATURE:
<223> OTHER INFORMATION: mutated Neomycin phosphotransferase gene

<400> SEQUENCE: 26
atgattgaac aagatggatt gcacgcaggt tctccggccg cttgggtgga gaggctattc       60
ggctatgact gggcacaaca gacaatcggc tgctctgatg ccgccgtgtt ccggttgtca      120
gcgcaggggc gcccggttct ttttgtcaag accgacttgt ccggtgcctt gaatgaattg      180
caggacgagg cagcgcggct atcgtggttg gccacgacgg gcgttccttg cgcagctgtg      240
ctcgacgttg tcactgaagc gggaagggac tggttgctat tgggcgaagt gccggggcag      300
gatctcttgt catctcacct tgctcctgcc gagaaagtat ccatcatggc tgatgcaatg      360
cggcggttgc atacgcttga tccggctacc tgcccattcg accaccaagc gaaacatcgc      420
atcgagcgag cacgtactcg gatggaagcc ggtcttgtcg atcaggatga tttggacgaa      480
```

```
                                              -continued gagcatcagg ggctcgcgcc agccgaattg ttcgccaggc tcaaggcgcg catgcccgac      540
ggcgaggatc tcgtcgtgac ccatggcgat gcctgcttgc cgaatatcat ggtggaaaat      600
ggccgctttt ctggattcat cgactgtggc cggttgggtg tggcggaccg ctatcaggac      660
atagcgttgg ctacccgtga tattgctgaa gagcttggcg gcgaatgggc tgaccgcttc      720
ctcgtgcttt acggtatcgc cgctcccgat tcgcagcgca tcgccttcta tcgccttctt      780
gacgagttct tctga                                                       795
```